US00PP14516P29

(12) United States Plant Patent
Slaughter et al.

(10) Patent No.: US PP14,516 P2
(45) Date of Patent: Feb. 10, 2004

(54) NECTARINE TREE NAMED 'BURNECTNINE'

(50) Latin Name: *Prunus persica*
Varietal Denomination: Burnectnine

(75) Inventors: John K. Slaughter, Clovis, CA (US); Timothy J. Gerdts, Kingsburg, CA (US)

(73) Assignee: The Burchell Nursery, Inc., Oakdale, CA (US)

( * ) Notice: Subject to any disclaimer, the term of this patent is extended or adjusted under 35 U.S.C. 154(b) by 57 days.

(21) Appl. No.: 10/346,864

(22) Filed: Jan. 17, 2003

(51) Int. Cl.[7] ..... A01H 5/00
(52) U.S. Cl. ..... Plt./188
(58) Field of Search ..... Plt./188

*Primary Examiner*—Bruce R. Campell
*Assistant Examiner*—Susan B. McCormick
(74) *Attorney, Agent, or Firm*—Wells St. John P.S.

(57) ABSTRACT

A new and distinct variety of nectarine tree (*Prunus persica* sub species *nuciperisica*), and which has been denominated varietally as 'Burnectnine', and which produces an attractively colored white-fleshed, aromatic, clingstone nectarine, which is mature for harvesting and shipment approximately June 4 to June 11 under ecological conditions prevailing in the San Joaquin Valley of Central California.

1 Drawing Sheet

BACKGROUND OF THE NEW VARIETY

The present invention relates to a new, novel and distinct variety of nectarine tree, *Prunus persica* (subspecies *nuci-persica*), which has been denominated varietally as 'Burnectnine'.

ORIGIN

The present variety of nectarine tree resulted from an on-going program of fruit and nut tree breeding. The purpose of this program is to improve the commercial quality of deciduous fruit and nut varieties, and rootstocks, by creating and releasing promising new selections of prunus, malus and regia species. To this end we make both controlled and hybrid cross pollinations each year in order to produce seedling populations from which improved progenies are evaluated and selected.

The seedling 'Burnectnine' was originated by us from a population of seedlings grown in our experimental orchards located near Fowler, Calif. The seedlings, grown on their own roots, were the result of a controlled cross of the yellow-fleshed 'Grand Diamond' nectarine tree (U.S. Plant Pat. No. 4,095), which was used as the seed parent, and an acidic, white-fleshed nectarine tree, 'G3.006' (unpatented) which was used as the pollen parent. One seedling, which is the present variety, exhibited especially desirable characteristics, and was designated as 'B17.011', and was marked for subsequent observation. After the 1996 growing season, the new variety was selected for advanced evaluation and repropagation.

A SEXUAL REPRODUCTION

Asexual reproduction of this new and distinct variety of nectarine tree was accomplished by budding the new nectarine tree variety to 'Nemaguard' Rootstock (non-patented). This was performed by us in our experimental orchard which is located near Fowler, Calif. Subsequent evaluations have shown those asexual reproductions run true to the original tree. All characteristics of the original tree, and its fruit, were established and appear to be transmitted through succeeding asexual propagations. We have observed fruit for the past 6 successive years from approximately 15 propagated trees.

SUMMARY OF THE VARIETY

'Burnectnine' is a new and distinct variety of nectarine tree, which is of large size, and which has vigorous growth. The new nectarine tree variety is also a regular and productive bearer of relatively large, firm, acidic, white fleshed, aromatic and clingstone fruit which have good flavor, and eating quality. The tree of the present variety has a medium-high chilling requirement of approximately 700 hours. Still further this tree also produces relatively uniformly sized fruit throughout the tree and which have a high degree of red skin coloration, and a firm flesh. The fruit of this new tree also appears to have good handling and shipping qualities. Moreover, the 'Burnectnine' Nectarine tree bears fruit which are ripe for commercial harvesting and shipment on approximately June 4 to June 11 under the ecological conditions prevailing in the San Joaquin Valley of central California. In relative comparison to the 'Grand Diamond' nectarine tree, which is the seed parent, the fruit of the 'Burnectnine' nectarine tree ripens about 12 to 14 days earlier and further is white fleshed.

BRIEF DESCRIPTION OF THE DRAWING

The accompanying drawing, which is provided, is a color photograph of the present variety. It depicts two whole mature fruit, and one fruit dissected substantially in the equatorial plane, and viewed from the apical perspective to reveal the flesh color and the stone thereof. The external coloration of the fruit is shown sufficiently matured for harvesting and shipment. Additionally the photograph displays a vegetative shoot bearing typical leaves. The colors in this photograph are as nearly true as is reasonably possible in a color representation of this type. Due to chemical development, processing, and printing, the leaves and fruit depicted in these photographs may or may not be accurate when compared to the actual specimen. For this reason, future color references should be made to the color plates (Royal Horticultural Society) and descriptions provided.

DETAILED DESCRIPTION

Referring more specifically to the pomological details of this new and distinct variety of nectarine tree, the following was observed during the sixth fruiting season under the ecological conditions prevailing at orchards located near the town of Fowler, county of Fresno, state of California. All major color code designations are by reference to The R.H.S. Colour Chart (Fourth Edition) provided by The Royal Horticultural Society of Great Britain.

Tree:

*Size.*—Generally — Considered medium large as compared to other common commercial nectarine cultivars ripening in the early to mid-season of maturity. The tree of the present variety was pruned to a height of approximately 280.0 cm to about 305.0 cm at maturity.

*Vigor.*—Considered vigorous. The present nectarine tree variety grew from about 149.0 cm to 164.0 cm in height during the first growing season. The new variety was pruned to a height of approximately 140.6 cm during the first dormant season and primary scaffolds were then selected for the desired tree structure.

*Productivity.*—Productive. Fruit set varies from twice to several times more than the desired crop load. Fruit set is spaced by thinning to develop the remaining fruit into the desired market size. The number of fruit set varies with the prevailing climatic conditions, and cultural practices during the bloom period and is therefore not distinctive of the variety.

*Bearer.*—Regular. Fruit set has been heavy, and thinning was necessary during the past 6 years.

*Form.*—Upright, and pruned to a vase shape.

*Density.*—Considered medium dense. It has been discovered that pruning the branches from the center of the tree to obtain a resulting vase shape allows for air movement and appropriate amounts of sunlight to enhance fruit color and renewal of fruiting wood throughout the tree.

*Hardiness.*—The present tree was grown and evaluated in USDA Hardiness Zone 9. The winter chilling requirements of the new tree are approximately 750 hours below 7.0 degrees C. The new variety also appears to be hardy under typical Central San Joaquin Valley climatic conditions.

Trunk:

*Diameter.*—Approximately 12.5 cm in diameter when measured at a distance of approximately 15.24 cm above the soil level, at the end of the sixth growing season.

*Bark texture.*—Considered moderately rough, with numerous folds of papery scarfskin being present.

*Lenticels.*—Numerous flat, oval lenticels are present. The lenticels range in size in size from approximately 4.0 to about 7.0 millimeters in width, and from 1.0 to about 2.0 millimeters in height.

*Lenticel color.*—Considered an orange brown, (RHS Greyed Orange Group N167 C).

*Bark coloration.*—Variable, but it is generally considered to be a brown color, (RHS Greyed-Orange Group 166 A).

Branches:

*Size.*—Considered average for the variety.

*Diameter.*—Average as compared to other varieties. The branches have a diameter of about 6.1 centimeters when measured during the sixth year after grafting.

*Surface texture.*—Average, and appearing furrowed on wood, which is several years old.

*Crotch angles.*—Primary branches are considered variable and between about 46 to 54 degrees from the horizontal axis. This characteristic is not considered distinctive of the variety, however.

*Current season shoots.*—Surface texture — Substantially glabrous.

*Internode length.*—Approximately 2.3 to about 2.6 cm.

*Color of mature branches.*—Medium brown, (RHS Greyed Orange Group 176 C).

*Current seasons shoots.*—Color — Light green, (RHS Yellow Green Group N144 B). The color of new shoot tips is considered a bright and shiny green (RHS Green Group 143 B).

Leaves:

*Size.*—Considered medium for the species. Leaf measurements have been secured from vigorous, upright, current-season growth taken at approximately mid-shoot.

*Leaf length.*—Approximately 132.0 to about 135.0 millimeters.

*Leaf width.*—Approximately 35.0 to about 40.0 millimeters.

*Leaf base shape.*—Slightly oblique relative to the leaf longitudinal axis.

*Leaf form.*—Lancelolate.

*Leaf tip form.*—Acuminate.

*Leaf color.*—Dark green, (approximately RHS Green Group 137 A).

*Leaf texture.*—Glabrous.

*Lower leaf surface color.*—Medium green, (RHS Green Group 137 C).

*Leaf venation.*—Pinnately veined.

*Mid-vein.*—Color — Light yellow green, (RHS Yellow Green Group 145 C).

*Leaf margins.*—Slightly undulating. Form — Considered crenate, and occasionally doubly crenate. Uniformity — Considered generally uniform.

*Leaf petioles.*—Size — Considered medium. Length — about 7.0 to about 10.0 mm. Diameter — about 2.0 to about 2.5 mm. Color — Pale green, (RHS Green Group 143 C).

*Leaf glands.*—Size — Moderately small, about 1.0 mm in height, and about 2.0 mm in width. Number — Generally one per side, occasionally two per side. Type — Reniform, and considered reasonably unappressed relative to the petiole margin. Color — Orange brown, (RHS Grey Brown Group N199 C).

*Leaf stipules.*—Size — Medium for the variety. Number — Typically 2 per leaf bud and up to 6 per shoot tip. Form — Lanceolate in form and having a serrated margin. Color — Green, (RHS Green Group 141 B) when young, but graduating to a brown color, (RHS Greyed Orange group 166 C) with advancing senescence. The stipules are considered to be early deciduous.

Flowers:

*Flower buds.*—Generally — The floral buds, depending upon the stage of development, are approximately 6.0 millimeters wide; and about 10.0 millimeters long; conic in form; and slightly appressed relative to the bearing shoot.

*Flower buds.*—Color — The bud scales are reddish-brown, (approximately RHS Greyed Purple Group 183 B). The buds are considered hardy under typical central San Joaquin Valley climatic conditions.

*Hardiness.*—No winter injury has been noted during the last several years of evaluation in the central San Joaquin Valley. The current variety has not been intentionally subjected to drought or heat stress and therefore this information is not available.

*Date of first bloom.*—Mar. 1, 2002.

*Blooming time.*—Considered mid-season in relative comparison to other commercial nectarine cultivars grown in the central San Joaquin Valley. Date of full bloom was observed on Mar. 7, 2002. The date of bloom varies slightly with the prevailing climatic conditions and cultural practices.

*Duration of bloom.*—Approximately 11 days. This characteristic varies slightly with the prevailing climatic conditions.

*Flower type.*—The variety is considered to have a showy type flower.

*Flower size.*—Flower diameter at full bloom is approximately 40.0 to about 43.0 millimeters.

*Bloom quantity.*—Considered abundant.

*Flower bud frequency.*—Normally 1 to 2 flower buds appear per node.

*Petal size.*—Generally — Considered large for the species. Length — Approximately 20.0 to about 22.0 millimeters. Width — Approximately 18.0 to about 21.0 millimeters.

*Petal form.*—Rotund.

*Petal count.*—Nearly always 5.

*Petal texture.* —Glabrous.

*Petal color.*—Variable, from a light pink, (RHS Red Purple Group N57 D) to a medium pink, (RHS Red Purple Group N57 C).

*Fragrance.*—Slight.

*Petal claw.*—Form — The claw is considered truncate and has a medium size when compared to other varieties. Length — Approximately 7.0 to about 9.0 millimeters. Width — Approximately 6.0 to about 7.0 millimeters.

*Petal margins.*—Generally considered variable, from nearly smooth, to moderately undulate.

*Petal apex.*— Generally — The petal apices generally appear entire with the apical groove.

*Flower pedicel.*—Length — Considered medium-long, and having an average length of approximately 4.0 to about 5.0 millimeters. Diameter — Considered average, approximately 2.0 millimeters. Color — A medium brown, (RHS Greyed Red Group 178 B).

*Floral nectaries.*—Color — A pale green, (RHS Yellow Green Group N144 A).

*Calyx.*—Surface Texture — Generally glabrous. Color — A dull red, (approximately RHS Greyed Purple Group 183 A).

*Sepals.*—Surface Texture — The surface has a short, fine, pubescent texture. Size — Average, and ovate in form. Color — A dark reddish purple, (approximately RHS Greyed Purple Group 187 A).

*Anthers.*—Generally — Large in size. Color — Reddish purple, (approximately RHS Greyed Purple Group 187 C).

*Pollen production.*—Pollen is abundant, and has a yellow color, (approximately RHS Yellow Group 12 A).

*Filaments.*—Size — Variable in length, approximately 17.0 to about 19.0 millimeters. Color — Considered a pale pink, (RHS Red Purple Group 62 D).

*Pistil.*—Number — Usually 1, rarely 2. Generally — Average in size. Length — Approximately 16.0 to about 19.0 millimeters including the ovary. Color — Considered pale green, (approximately RHS Yellow Green Group 145 B). Surface Texture — The variety has a long glabrous pistil.

Fruit:

*Maturity when described.*— Firm ripe condition (shipping ripe). Date of first picking — Jun. 4, 2002. Date of last picking — Jun. 13, 2002. The date of harvest varies slightly with climatic conditions.

*Size.*—Generally — Considered relatively large, and uniform.

*Average cheek diameter.*—Approximately 76.0 to about 78.0 millimeters.

*Average axial diameter.*—Approximately 72.0 to about 75.0 millimeters.

*Typical weight.*—Approximately 231.0 grams. This characteristic is highly dependent upon the prevailing cultural practices and therefore is not particularly distinctive of the variety.

*Fruit form.*—Generally — Moderately oblate. The fruit is generally uniform in its symmetry.

*Fruit suture.*—Shallow, and extending from the base to the apex. No apparent callousing or stitching exists along the suture line.

*Suture.*—Color — The background color appears to be white, (approximately RHS White Group 155 C), and occasionally some red coloration is evident, (approximately RHS Red Group 46 C).

*Ventral surface.*—Form — Slightly indented.

*Apex.*—Rounded.

*Base.*—Retuse.

*Stem cavity.*—Rounded and relatively shallow. The average depth of the stem cavity is about 1.62 cm. The average width of the stem cavity is about 1.86 cm.

*Fruit skin.*—Thickness — Considered medium in thickness, and tenacious to the flesh. Texture — Short, fine, and glabrous. Taste — Non-astringent. Tendency to crack — No cracking has been observed. Occasional russeting can be observed.

*Blush color.*—The red blush color is variable from a reddish orange, (approximately RHS Red Group 42 B), to a dark red, (approximately RHS Red Group 46 A). The blush color ranges from about 75% to about 95% of the fruit surface depending upon the sunlight exposure and the prevailing growing conditions. Ground Color — Generally a yellow-white, (approximately RHS White Group 155 D).

*Fruit stem.*—Moderate in length, approximately 6.0 to about 7.0 millimeters. Diameter — Approximately 2.0 to about 3.0 millimeters. Color — A brown, (approximately RHS Greyed Orange Group 164 C).

*Flesh.*—Ripens — Evenly. Texture — Firm, and dense. Considered melting. Fibers — Few, small, and tender ones may be found. Aroma — Very fragrant. Considered aromatic. Eating Quality — Very good. Flavor — Considered sweet and acidic in flavor. The flavor is considered both pleasant and balanced.

Juice Production — Moderate. Brix — About 14.5 degrees. This characteristic varies slightly with the number of fruit per tree; the prevailing cultural practices; and the surrounding climatic conditions. Flesh Color — Pale white, (approximately RHS White Group 155 D).

Stone:

*Type.*—Clingstone.

*Size.*—Considered medium large for the variety. The stone size varies with prevailing crop load and tree vigor, and is therefore not characteristic of the variety.

*Length.*—Average, about 25.5 to about 27.0 millimeters.

*Width.*—Average, about 22.0 to about 24.0 millimeters.

*Diameter.*—Average, about 17.0 to about 21.0 millimeters.

*Form.*—Obovoid.

*Base.*—The stone is usually oblique relative to the stone's vertical axis.

*Apex.*—Shape — The stone apex is raised and has an acute, protruding tip.

*Stone surface.*—Surface Texture — Irregularly furrowed toward apex, and pitted toward the base. The stone exhibits substantial grooving laterally. Substantial grooving over the apical shoulders is normally evident. Surface pitting is more prominent generally, and noted more frequently in the mid-section of the stone. Ridges — The surface texture varies from sharp to rounded. Ventral Edge — Width — Considered medium, and having a dimension of approximately 2.0 to about 4.0 millimeters at the mid-suture. The wings are most prominent over the suture line. Dorsal Edge — Shape — Full, heavily grooved, and having jagged edges. The dorsal edge is significantly eroded over the apical shoulder.

*Stone color.*—(Approximately RHS Orange White Group 159 D).

*Tendency to split.*—Occasional splits have been observed.

*Kernel.*—Size — Kernel is considered average. Length — Approximately 20.0 millimeters. Width — Approximately 12.0 millimeters Thickness — Approximately 4.0 millimeters. Form — Considered ovoid. Pellicle — Pubescence. Color — Considered to be a pale brown (Greyed Orange Group N167 B).

*Use.*—The new nectarine tree variety 'Burnectnine' is considered to be a tree of the early to mid-season of maturity, and which produces fruit which are considered firm, attractively colored, and which are useful for both local and long distance shipping.

*Keeping quality.*—Excellent. Fruit has stored well up to 25 days after harvest at about 1.0 degree Celsius.

*Shipping quality.*—Good. The fruit produced by the new tree showed minimal bruising of the flesh or other skin damage after being subjected to normal harvesting and packing procedures.

*Resistance to insects and disease.*—No particular susceptibilities were noted. The present variety has not been tested to expose or detect any susceptibilities or resistances to any known plant and/or fruit diseases.

Although the new variety of nectarine tree possesses the described characteristics when grown under the ecological conditions prevailing near Fowler, Calif., in the central part of the San Joaquin Valley of California, it should be understood that variations of the usual magnitude and characteristics incident to changes in growing conditions, fertilization, pruning, pest control and horticultural management are to be expected.

Having thus described and illustrated our new variety nectarine tree, what we claim is new and desire to secure by Plant Letters Patent is:

1. A new distinct variety of nectarine tree, substantially as illustrated and described, and which is characterized principally as to novelty by producing an attractively colored white-fleshed, clingstone nectarine which is mature for harvesting and shipment approximately June 4 to June 11 under the ecological conditions prevailing in the San Joaquin Valley of Central California.

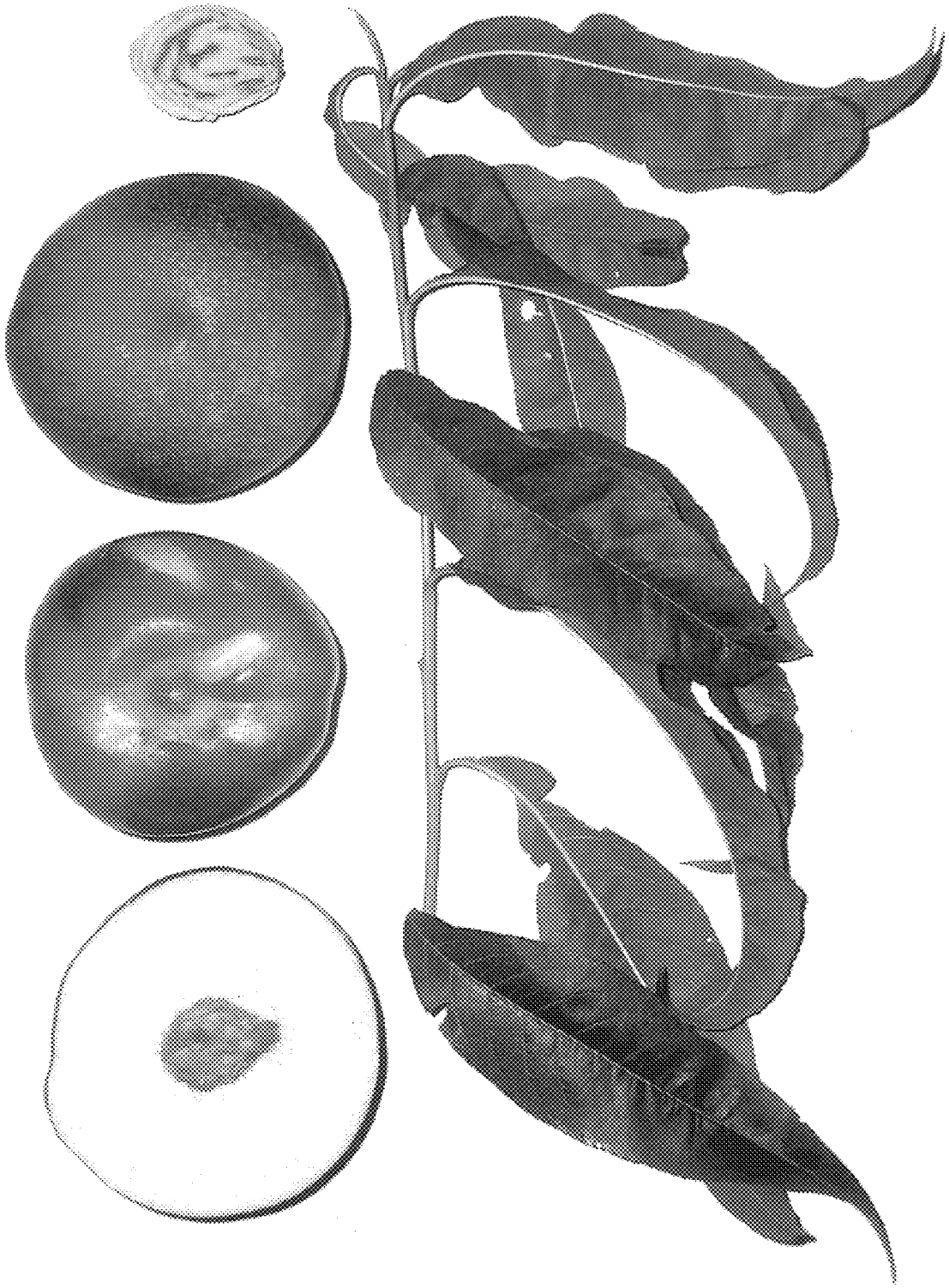

* * * * *